United States Patent [19]

Ladov et al.

[11] 4,198,207
[45] Apr. 15, 1980

[54] DETERMINATION OF WATER CONTENT IN PRESENCE OF OILS

[75] Inventors: Edwin N. Ladov, Cherry Hill; Derek A. Law, Pitman; Guenter H. Kuehl, Cherry Hill, all of N.J.

[73] Assignee: Mobil Oil Corporation, New York, N.Y.

[21] Appl. No.: 24,233

[22] Filed: Mar. 26, 1979

[51] Int. Cl.[2] .................. G01N 25/56; G01N 33/18; G01N 33/28
[52] U.S. Cl. .......................... 23/230 HC; 23/230 R; 73/61.1 R
[58] Field of Search ............... 23/230 R, 230 HC; 73/73, 61.1 R

[56] References Cited

U.S. PATENT DOCUMENTS

| | | | |
|---|---|---|---|
| 3,528,775 | 9/1970 | O'Hara et al. | 23/230 HC |
| 3,833,340 | 9/1974 | Jones et al. | 23/230 HC |
| 3,873,271 | 3/1975 | Young et al. | 23/230 HC |
| 4,089,652 | 5/1978 | Pedersen | 23/230 R X |
| 4,116,045 | 9/1978 | Potter | 23/230 HC |

Primary Examiner—R. E. Serwin
Attorney, Agent, or Firm—Charles A. Huggett; Raymond W. Barclay; Claude E. Setliff

[57] ABSTRACT

The invention deals with the determination of water content in presence of oils, as, for example, oil- and water-containing emulsions, using zeolites and the temperature rise caused upon adsorption of water as the basis.

7 Claims, 1 Drawing Figure

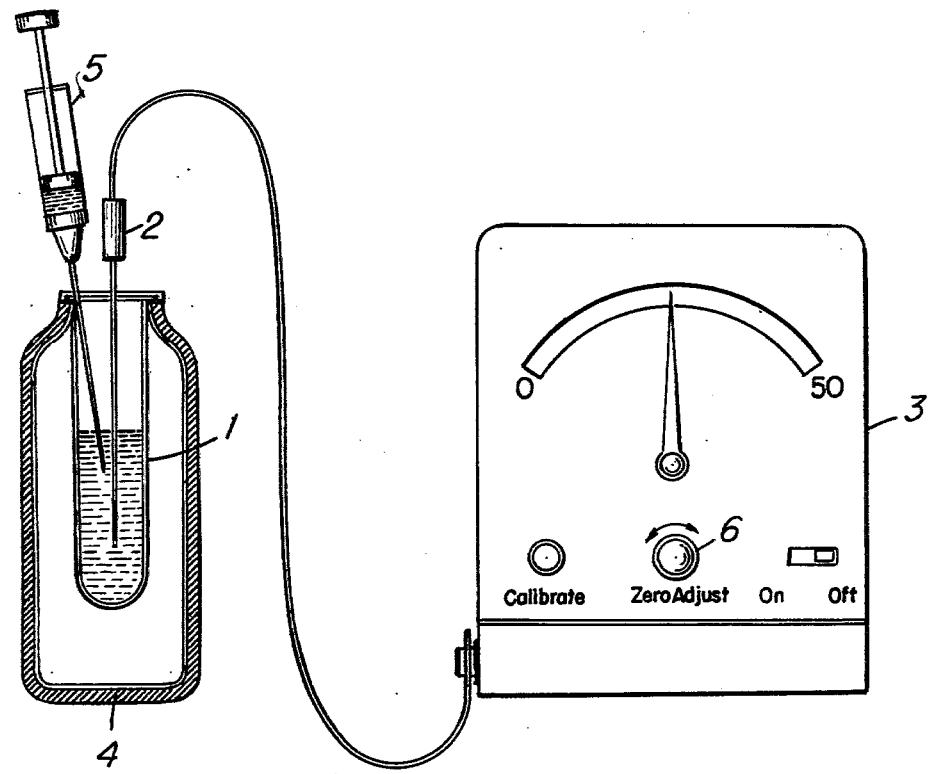

DETERMINATION OF WATER CONTENT IN PRESENCE OF OILS

The work leading to the invention described herein was done under a government contract.

BACKGROUND OF THE INVENTION

Field of the Invention

The invention relates to a method for determining water in presence of oils. More particularly, it is concerned with determining water in such systems employing a zeolite.

The Figure

The FIGURE is a schematic of the apparatus used in determining water content in fluid systems.

Discussion of the Prior Art

Current methods for water determination are time-consuming, difficult to run and expensive. One method that has been used for many years is the Karl Fischer method, described in one of its aspects in ASTM D1744-64(1968). Basically, this procedure involves the titration of the liquid petroleum product to be analyzed with Karl Fischer reagent, as described in D1744.

Other methods include distillation and the use of, for example, anhydrous sodium sulfate or concentrated sulfuric acid. The determination of water content with the latter two reagents is made by measuring the temperature rise due to heat of solution. While the same principle is found with the use of zeolite, i.e. measurement of temperature rise as a function of the amount of water present, it is believed that the use of zeolites is unobvious. The method using zeolites is extremely accurate and selective, permitting rapid determination of water in systems wherein the amount of water occurs over a wide range.

U.S. Pat. No. 3,528,775 and 4,089,652 disclose methods for determining water in oils.

SUMMARY OF THE INVENTION

In accordance with the invention there is provided a method for determining the amount of water in the presence of an oil which comprises adding a zeolite to a sample to be tested and determining the amount of water as a function of the rise in temperature produced.

DESCRIPTION OF SPECIFIC EMBODIMENTS

The invention described herein is applicable to several different systems containing water and oil. For example, during the operation of a marine diesel engine, the circulating lubricant generally becomes contaminated with water. The effective working life of the lubricant is limited by the accumulation of water, which, apart from altering the lubricant properties of the oil, may have a deleterious effect on the metal to be lubricated. Similar considerations arise with other uses of oils.

In order to determine whether the oil is suitable for further use or for regeneration, or for rejection, it is frequently necessary to know whether water is present in the oil in excess of a predetermined tolerated proportion. Such a proportion might be in the region of a few percent, e.g. 1 to 5 percent by weight of wet lubricant, but substantially higher water contents can be encountered. On the other hand, it may be desired to apply a more stringent standard of a fraction of one percent.

Devices are known by means of which the water content of an oil can be determined. For instance, a measured amount of oil may be confined in a closed vessel incorporating a pressure gauge together with a substance which reacts with water to produce gas. The amount of water present in the oil is then determined according to the pressure rise shown on the gauge. The oil may also be contacted in a vessel with a water-reactive substance and a carrier. The amount of gas produced is then measured by means of a separate manometer U-tube equipped with another manometric liquid and connected to the vessel, measuring the internal pressure developed.

Further, in the maintenance of Diesel engines, such as those used on railroad locomotives, it is generally recognized that the water content of the lubricating oil should be kept below about 0.45% to 0.5% by weight to minimize damage to the moving parts of the engine. Trace quantities of dispersed water in aviation fuels can have serious consequence as such water may accumulate in the float bowl of the carburetor and result in engine failure particularly at high altitudes and low temperatures where carburetor icing may occur. Water that is present in aviation jet fuels freezes to form ice crystals at the low temperatures encountered in high altitude operations. Such ice crystals may block the fuel lines and fuel jets. Transformer oil is another petroleum product, the performance of which is adversely effected by the presence of trace amounts of moisture.

Also, there are numerous applications for water-in-oil or oil-in-water emulsions. Notable among such applications are the hydraulic oils. In view of the wide use of hydraulic oils, as for instance in automobiles, airplanes and various industrial areas, such as mining, there is a serious need for an accurate, selective and rapid analytical method for determining water.

Many methods have been developed for the quantitative determination of water, but such procedures, in general, must be carried out in well-equipped laboratories, using sophisticated equipment. If one requires immediate, on the spot, information with respect to the water content of a particular petroleum product, there is not sufficient time to transmit samples to a distant laboratory and wait for a report from a chemical analyst. The present invention eliminates this time consuming analysis by allowing a simple apparatus to be set up at the desired site for essentially instantaneous determinations of water.

The invention as described herein deals particularly with emulsions used in hydraulic systems, but it is not limited thereto.

According to the present invention, the mixture of solvent and crystalline aluminosilicate zeolite will contain from about 0.1 part to about 5 parts of zeolite per part of solvent. From about 0.1 part to about 10 parts of fluid to be tested per part of total mixture of solvent and zeolite are injected into the mixture which is sealed in a vial inside a vacuum flask (Dewar-type). The parts given are by weight.

The apparatus for detecting water in the oil by this method consists of the vacuum flask and presealed glass disposable reaction tube with a septum lid, an injection syringe and an electrical instrument (analyzer) comprising a thermistor probe for insertion into the reaction tube to measure the increase in temperature.

The electrical instrument used herein was calibrated so as to read directly in percent water as a function of temperature by inserting the thermistor probe of the analyzer into a heated water bath and then scaling accordingly.

The preferred zeolite is zeolite 4A because of its large exotherm on adsorption of water. However, other zeolites may be used. Among them are included zeolites 3A, 5A, 10A and 13X. The amount of heat generated and the rate at which this heat is generated will vary from zeolite to zeolite.

Solvents are used to permit good contact between the test emulsion and solid reactant and to limit the temperature rise to reasonable and safe levels, i.e. the rise should not exceed about 130° F. Among the useful solvents are Stoddard Solvent (a mixed aromatic fluid) and isooctane. These solvents are for use with oil-miscible emulsions. However, the method applies to other fluids such as water-glycols systems or to soluble oils. In these cases the "solvent" should be water-miscible, including alcohols, ketones and the like. Large-pore zeolites are not recommended for water-miscible systems; they should be restricted to 3A, 4A and other small-pore zeolites.

The oils that may be employed in the method of the invention include petroleum products of lubricating viscosity and synthetic fluids. Of the latter class may be included synthetic ester lubricants, such as those formed from monohydric alcohol and dicarboxylic acids, glycols or glycerols with monocarboxylic acids, and pentaerythritols with carboxylic acids, including alcohols having from about 4 to 20 carbons, and carboxylic acids having from about 2 to about 18 carbon atoms. Many synthetic esters may have mixed alcohols or carboxylic acids. Commonly may be included 2-ethylhexyl sebacate, trimethylolpropane trioctanoate, and especially pentaerythritol esters of valeric acid, isovaleric acid, caproic acid, caprylic acid, pelargonic acid, capric acid, and the like. Of special interest is a mixed pentaerythritol ester of an equimolar proportion of commercial valeric acid (containing isovaleric acid) and pelargonic acid. Other synthetic fluids include liquid polyolefins, alkylene oxide fluids, silicone fluids, polyacetals, and simple hydrocarbons of stable fluid viscosities. The method is also effective with hydrocarbon fuels.

Having disclosed the invention in general, the following will illustrate it. It will be understood that the Examples that follow are illustrative only and are not meant to limit the scope of the invention.

EXAMPLE 1

The numbers in this Example refer to the FIGURE.

Five grams of zeolite 4A and 10 grams of isooctane were premixed in a small 24 ml. capacity reaction tube with a septum lid (1). A thermistor (2) from the water analyzer (3) was inserted into the reaction tube which had been placed inside an insulated chamber (a Dewar-type flask) (4). 2 ml. of a water-in-oil emulsion containing 43% by weight of water was injected into the tube with a syringe (5). The entire assembly was shaken for 30 seconds and the percent water determined as amount of temperature rise above ambient.

It was determined that the sample contained 43± 1% by weight of water.

Prior to making the determination of this Example (and of those that follow), the meter was calibrated at 43% water by running a sample known to contain that amount of water. The zero adjust knob (6) was used to zero the meter for the fluid ambient temperature before adding sample.

EXAMPLE 2

This example is a comparison of the results obtained using this method with those obtained using Karl Fischer reagent.

Using substantially the procedure of Example 1, 11 grams of Stoddard Solvent and 11 grams of zeolite 4A were mixed and placed in the reaction tube and three ml. of emulsion was injected into the tube. After shaking for 30 seconds, the results shown in Table 1 were obtained.

The same emulsion was tested for water by the standard Karl Fischer method. The results are also shown in Table 1.

TABLE 1

| Emulsion | Wt. Percent Water | |
|---|---|---|
| | This Invention | Karl Fischer |
| A | 43.0 | 43.0 |
| B | 32.0 | 31.4 |
| C | 42.8 | 42.5 |
| D | 43.0 | 43.0 |

Emulsions A, B and C - Commercially available emulsions
Emulsion D - a hydraulic fluid comprising 100" paraffinic neutral mineral oil, water, ethylene glycol and an additive package.

We claim:

1. A method of determining water in the presence of an oil which comprises
   (a) bringing a sample of oil and water into contact with a mixture of solvent and crystalline aluminosilicate zeolite whereby the water adsorption causes a rise in temperature,
   (b) providing a means for measuring the temperature rise in terms of percentage by weight of water and
   (c) determining the percentage of water in the sample.

2. The method of claim 1 wherein the solvent is a mixed aromatic fluid.

3. The method of claim 1 wherein the solvent is isooctane.

4. The method of claim 1 wherein the mixture in (a) contains from about 0.1 part to about 5 parts of crystalline aluminosilicate zeolite per part of solvent.

5. The method of claim 1 wherein the mixture in (a) contains from about 0.1 part to about 10 parts of oil and water sample per part of the mixed solvent and zeolite.

6. The method of claim 1 wherein the oil is a mineral oil.

7. The method of claim 1 wherein the oil is a synthetic oil.

* * * * *